(12) United States Patent
Zipplies et al.

(10) Patent No.: US 10,744,497 B2
(45) Date of Patent: Aug. 18, 2020

(54) METHOD FOR REMOVING PERFLUORINATED ALKANOIC ACIDS

(71) Applicant: 3M INNOVATIVE PROPERTIES COMPANY, St. Paul, MN (US)

(72) Inventors: Tilman C. Zipplies, Burghausen (DE); Klaus Hintzer, Kastl (DE); Helmut Traunspurger, Julbach (DE); Karl D. Weilandt, Meerbusch (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 59 days.

(21) Appl. No.: 16/081,808

(22) PCT Filed: Mar. 2, 2017

(86) PCT No.: PCT/US2017/020473
§ 371 (c)(1),
(2) Date: Aug. 31, 2018

(87) PCT Pub. No.: WO2017/151935
PCT Pub. Date: Sep. 8, 2017

(65) Prior Publication Data
US 2019/0070599 A1 Mar. 7, 2019

Related U.S. Application Data

(60) Provisional application No. 62/303,577, filed on Mar. 4, 2016.

(51) Int. Cl.
| | | |
|---|---|---|
| *C08F 6/16* | (2006.01) |
| *B01J 41/05* | (2017.01) |
| *C07C 51/47* | (2006.01) |
| *B01J 20/26* | (2006.01) |
| *C07C 51/08* | (2006.01) |
| *C02F 1/42* | (2006.01) |
| *B01J 47/02* | (2017.01) |
| *C02F 101/36* | (2006.01) |
| *C07C 55/32* | (2006.01) |
| *C07C 59/135* | (2006.01) |

(52) U.S. Cl.
CPC ............. *B01J 41/05* (2017.01); *B01J 20/267* (2013.01); *B01J 47/02* (2013.01); *C02F 1/42* (2013.01); *C07C 51/08* (2013.01); *C07C 51/47* (2013.01); *C08F 6/16* (2013.01); *C02F 2001/422* (2013.01); *C02F 2101/36* (2013.01); *C07C 55/32* (2013.01); *C07C 59/135* (2013.01)

(58) Field of Classification Search
CPC .......... B01J 41/05; B01J 20/267; B01J 47/02; C07C 51/08; C07C 51/47; C02F 1/42; C08F 6/16
See application file for complete search history.

(56) References Cited

U.S. PATENT DOCUMENTS

| | | | |
|---|---|---|---|
| 3,882,153 A | 5/1975 | Seki | |
| 4,282,162 A * | 8/1981 | Kuhls | C07C 51/47 554/185 |
| 5,442,097 A | 8/1995 | Obermeier | |
| 6,437,159 B1 * | 8/2002 | Schultz | C07C 51/412 554/187 |
| 6,642,415 B1 * | 11/2003 | Fuhrer | B01J 41/04 562/602 |
| 2007/0025902 A1 * | 2/2007 | Hintzer | C08L 27/12 |
| 2007/0027251 A1 * | 2/2007 | Hintzer | C08L 27/12 524/544 |
| 2010/0000947 A1 * | 1/2010 | Koizumi | C02F 1/283 210/694 |
| 2012/0271065 A1 | 10/2012 | Haga | |
| 2014/0378734 A1 * | 12/2014 | Sumiya | G21F 9/12 588/18 |

FOREIGN PATENT DOCUMENTS

| | | |
|---|---|---|
| EP | 1069078 | 10/2014 |
| JP | 3-82999 * | 4/1991 |
| RU | 2319535 C2 | 3/2008 |
| WO | WO 2001-032563 | 5/2001 |
| WO | WO 2008-076746 | 6/2008 |

OTHER PUBLICATIONS

Deng, "Removal of perfluorooctane sulfonate from wastewater by anion exchange resins: Effects of resin properties and solution chemistry" Water Research, 2010, Ed.44, pp. 5188-5195.
Hintzer, "Handbook of Fluoropolymer Science and Technology, Fluoropolymer—Environmental Aspects Chapter 21" Wiley Interscience, 2014, pp. 495-496.
International Search report for PCT International Application No. PCT/US2017/020473 dated May 29, 2017, 5 pages.

* cited by examiner

*Primary Examiner* — Chester T Barry
(74) *Attorney, Agent, or Firm* — Thomas M. Spielbauer

(57) ABSTRACT

Provided are methods for removing a perfluorinated alkanoic acid from solutions containing the perfluorinated alkanoic acid and a fluorinated alkoxy acid. These methods include contacting the first solution with an anion-exchange resin to produce a second solution and a resultant anion-exchange resin having perfluorinated alkanoic acid adsorbed thereto, wherein the perfluorinated alkanoic acid is present in the first solution at a first concentration and is present in the second solution at a second concentration which is lower than the first concentration, and separating the second solution from the resultant anion-exchange resin.

15 Claims, No Drawings

METHOD FOR REMOVING PERFLUORINATED ALKANOIC ACIDS

CROSS REFERENCE TO RELATED APPLICATIONS

This application is a national stage filing under 35 U.S.C. 371 of PCT/US2017/020473, filed Mar. 2, 2017, which claims the benefit of Provisional Application No. 62/303, 577, filed Mar. 4, 2016, the disclosure of which is incorporated by reference in their entirety herein.

BACKGROUND

The aqueous emulsion polymerization and copolymerization of fluorinated, especially perfluorinated, monomers requires an emulsifier to stabilize the polymer particles in the liquid phase. Besides the ability to stabilize the particles and to prevent coagulation, the emulsifier should be inert under the polymerization conditions. In particular, emulsifiers that participate in chain transfer reactions should generally be avoided, as they tend to decrease the molecular weight of a polymer, whereas the desired molecular weight for fluoropolymers is usually quite high.

Accordingly, fluoropolymers have traditionally be polymerized in the presence of highly fluorinated or even perfluorinated emulsifiers, such as carboxylic and sulfonic acids and their salts, especially their ammonium salts.

While many materials may fulfil these requirements, industrial applications quickly converged upon the use of the ammonium salts of perfluorinated sulfonic acid (PFOS) and perfluorooctanoic acid (PFOA).

Over the last 25 years, however, an increasing number of scientific papers have been published detailing findings of PFOS and PFOA widely spread in the environment and in the blood of the general population. This environmental persistence and bioaccumulation has come under regulatory scrutiny. The United States Environmental Protection Agency (US-EPA) has held a number of hearings since 2000 regarding this material.

In May of 2000, 3M, decided to cease production of PFOS and PFOA. The phase out of PFOA was a challenge for the fluoropolymer industry, as there were very few alternative emulsifiers readily available to replace PFOS and PFOA.

In 2006, the US-EPA invited eight companies—including fluoropolymer manufacturers—to participate in a voluntary program to reduce global emissions of PFOA by 95% by 2010 and to work toward the elimination of PFOA by 2015. Meanwhile, PFOS and perfluorinated carboxylic acids with 11 to 14 carbon chain length are listed in Europe under its Regulation, Evaluation and Authorization of Chemicals (REACH) program as substances of very high concern (SVHC). It was also recommended to list PFOA as an SVHC under REACH.

SUMMARY

In one aspect, the present application relates to method for removing a perfluorinated alkanoic acid from a first solution containing the perfluorinated alkanoic acid and a fluorinated alkoxy acid. The method comprises contacting the first solution with an anion-exchange resin to produce a second solution and a resultant anion-exchange resin having perfluorinated alkanoic acid adsorbed thereto, wherein the perfluorinated alkanoic acid is present in the first solution at a first concentration and is present in the second solution at a second concentration which is lower than the first concentration. The method further comprises separating the second solution from the resultant anion-exchange resin.

In another aspect, the present application relates to a method for removing a perfluorinated alkanoic acid from a first solution containing the perfluorinated alkanoic acid and a fluorinated alkoxy acid, the method comprising contacting the first solution with an anion-exchange resin to produce a second solution and a resultant anion-exchange resin having perfluorinated alkanoic acid adsorbed thereto, wherein the perfluorinated alkanoic acid is present in the first solution at a first concentration and is present in the second solution at a second concentration which is lower than the first concentration. The method further comprises separating the second solution from the resultant anion-exchange resin. In this aspect, the perfluorinated alkanoic acid is selected from a perfluorinated alkyl carboxylic acid and a perfluorinated alkyl sulfonic acid.

In yet a further aspect, the present application relates to method for removing a perfluorinated alkanoic acid from a first solution containing the perfluorinated alkanoic acid and a fluorinated alkoxy acid. The method comprises contacting the first solution with an anion-exchange resin to produce a second solution and a resultant anion-exchange resin having perfluorinated alkanoic acid adsorbed thereto, wherein the perfluorinated alkanoic acid is present in the first solution at a first concentration and is present in the second solution at a second concentration which is lower than the first concentration. The method further comprises separating the second solution from the resultant anion-exchange resin. In this aspect, the perfluorinated alkanoic acid has from 4 to 12 carbon atoms.

DETAILED DESCRIPTION

Applicants have found that despite the voluntary phase-out, the regulatory attention, and the push by companies to find alternative emulsifiers; the environmental persistence, high water miscibility, and stability of PFOS and PFOA have meant that even samples of fluorinated alkoxy acids (which are frequently used as alternative emulsifiers) may be contaminated with perfluorinated alkanoic acids (such as PFOS and PFOA).

Applicants believe that such contaminations may arise from trace amounts of perfluorinated alkanoic acids remaining in the pipelines or storage tanks of facilities that have used such perfluorinated alkanoic acids in the past. Furthermore, Applicants believe they have observed formation of such perfluorinated alkanoic acids wholly unintentionally during emulsion polymerization processes. One potential source of these unintentionally formed perfluorinated alkanoic acids may be from perfluorinated vinylethers, which may generate reactive groups in the aqueous dispersion polymerization medium that grow by the addition, for instance, of tetrafluoroethylene, and are terminated with a sulfate radical (for instance, from an initiator). In particular, C4 to C12 perfluorinated alkanoic acids are highly stable and soluble in water, and may become solvated upon formation. These acids have then to be recovered from the aqueous emulsion polymerization medium, even in instances when they were not added to the reactor. It is believed that longer carbon-chain perfluorinated alkanoic acids may form as well, but that if present they may adhere to the dispersion particles, but are not soluble enough to be seen in the aqueous dispersion polymerization medium.

Accordingly, there exists an ongoing need to remove pefluorinated alkanoic acids from solutions containing a perfluorinated alkanoic acid and a fluorinated alkoxy acid.

Typical methods of removing perfluorinated alkanoic acids from solutions do not work in solutions that contain both perfluorinated alkanoic acid and fluorinated alkoxy acid. For instance, exposing a solution to an active carbon bed removes both perfluorinated alkanoic acid and fluorinated alkoxy acid. Further, distillation of derivatives of these acids (e.g., ester derivatives) is not practical due to the potential formation of azeotropes with impurities and the high purity requirements of the fluorinated alkoxy acids.

Surprisingly, the Applicants have found a method for removing preferentially a perfluorinated alkanoic acid from a solution containing a perfluorinated alkanoic acid and a fluorinated alkoxy acid.

Perfluorinated Alkanoic Acid

Perfluorinated alkanoic acids according to the present description are generally perfluorinated organic acids having a linear or branched alkyl group and an acid group (e.g., carboxylic acid, sulfonic acid, etc). Particularly, the perfluorinated alkanoic acid may be selected from a perfluorinated alkyl carboxylic acid and a perfluorinated alkyl sulfonic acid.

In a particular embodiment, the perfluorinated alkanoic acids include those having the general formula (I):

$$[R^1_f\text{-}A^-]X^+ \quad (I)$$

In formula (I), A represents an acid group (for instance, $-CO_2$ or $-SO_3$), $R^1_f$ represents a (i) linear or branched; (ii) fully fluorinated; (iii) alkyl group; that (iv) contains from 1 to 16 carbon atoms. More specifically, $R^1_f$ may contain from 4 to 12, from 6 to 12, from 8 to 12, or 8 or 9 carbon atoms. $X^+$ represents a cation (e.g., $H^+$, $Na^+$, $K^+NH_4^+$).

Specific embodiments include, for instance, perfluorooctanoic acid and perfluorooctane sulfonic acid.

Fluorinated Alkoxy Acid

Fluorinated alkoxy acids of the present description are generally perfluorinated or partially fluorinated organic acids having a linear or branched alkoxy group and an acid group (e.g., carboxylic acid, sulfonic acid, etc.). These fluorinated alkoxy acids may be used, for instance, as emulsifiers in the preparation of fluoropolymer dispersions, either as emulsifiers for dispersion polymerizations or as stabilizing additives/dispersing agents.

In a particular embodiment, the fluorinated alkoxy acids include those having the general formula (II):

$$[R_f\text{-}O\text{-}L\text{-}A^-]X^+ \quad (II)$$

In formula (II) A represents an acid group (for instance, $-CO_2$ or $-SO_3$), L represents a (i) linear, branched, or cyclic; (ii) partially or fully fluorinated; (iii) alkylene group or alkoxylene group (that is, a divalent carbon chain interrupted by one or more ether oxygen atoms); that (iv) contains from 1 to 10 carbon atoms. $R_f$ represents a (i) linear or branched; (ii) partially or fully fluorinated; (iii) alkyl group or alkoxy group (that is, a univalent carbon chain interrupted by one or more ether oxygen atoms); that (iv) contains from 1 to 10 carbon atoms. $X^+$ represents a cation (e.g., $H^+$, $Na^+$, $K^+$, $NH_4^+$).

In case the fluorinated alkoxy acid contains a partially fluorinated aliphatic group (e.g., either the L or $R_f$ group of general formula (II)), it is referred to as a partially fluorinated alkoxy acid. When the fluorinated alkoxy acid contains only perfluorinated aliphatic groups (e.g., both the L and $R_f$ groups of general formula (II)), it is referred to as a perfluorinated alkoxy acid.

In some embodiments, the molecular weight of the anionic part of the fluorinated alkoxy acid (i.e., excluding the weight of $X^+$) is less than 1,000 g/mole. In such instances, the number of carbon atoms in L and $R_f$ and the degree of fluorination in L and $R_f$ should be selected accordingly.

In specific embodiments, L is linear.

Specific examples of fluorinated alkoxy acids include, but are not limited to: $CF_3CF_2OCF_2CF_2OCF_2COOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, $CF_3CF_2CF_2OCF(CF_3)COOH$, $CF_3CF_2OCF_2CF_2OCF_2COOH$, $CF_3CF_2OCF_2CF_2CF_2COOH$, $CF_3OCF_2CF_2OCOOH$, and their ammonium and sodium salts.

First Solution

The first solution to be treated by the methods described herein, is generally an aqueous solution, meaning that water is the primary or only solvent. In some embodiments, secondary solvents (one that is present in a lesser amount than the main or primary solvent) may be present in minor amounts, intentionally added or arising, for instance, as impurities residual from the preparation of one or more of the components of the first solution.

The perfluorinated alkanoic acid may be present in the first solution in amounts ranging from trace to relatively high concentrations. In some embodiments, the perfluorinated alkanoic acid may be present in from 0.0001 weight percent (based on the total weight of the first solution) up to 10 weight percent (based on the total weight of the first solution). More specific ranges include from 0.001 weight percent to 1 weight percent, from 0.01 to 0.5 weight percent, or even from 0.05 to 0.5 weight percent.

Care must be taken with regard to the concentration of perfluorinated alkanoic acids in the first solution, as very high concentrations may lead to solubility issues, causing a phase separation of the perfluorinated alkanoic acid from the water phase. The upper limitation of the concentration of the perfluorinated alkanoic acid does not arise from any inherent limitation of the contacting or separating steps, but rather relate to the solubility of the perfluorinated alkanoic acid in the first solution. The lower limitation, similarly, does not arise from an inherent limitation of the contacting or separating steps, but rather relates to the state of the art detection limits of the available analytical techniques. Thus, one of ordinary skill in the art will understand that a proper upper concentration limit will depend on the specific identity of the selected perfluorinated alkanoic acid and a proper lower concentration limit will depend on the analytical method available for measurement.

Furthermore, it may be desirable to remove salts, such as those containing multivalent anions (e.g., sulfate and/or phosphate anions) from the first solution. Such salts, in particular such salts containing multivalent anions, can bind to the anion-exchange resin, thus reducing the capacity of the anion-exchange resin to participate in the contacting step described herein. One of ordinary skill in the art will understand that such salts may be removed by selecting the proper cation to elicit precipitation of the anions and further removal of the precipitant. For instance, sulfate anions can be removed by precipitation as a calcium, strontium or barium salt.

The pH of the first solution can affect the solubility of the perfluorinated alkanoic acid and/or the fluorinated alkoxy acid. Particularly, a pH in the range of 3 to 10, more specifically from 4 to 10, is expected to not adversely affect the solubility of the perfluorinated alkanoic acid and/or the fluorinated alkoxy acid. If the first solution is too acidic (pH below 3), the perfluorinated alkanoic acid and/or the fluorinated alkoxy acid may not be sufficiently soluble for the methods described herein.

The fluorinated alkoxy acid may be present in the first solution in amounts ranging from trace to relatively high concentrations. It may be present in a concentration higher than the concentration of the perfluorinated alkanoic acid or in a concentration lower than the perfluorinated alkanoic acid. In some embodiments, the fluorinated alkoxy acid may be present in from 0.0001 weight percent (based on the total weight of the first solution) up to 40 weight percent (based on the total weight of the first solution). More specific ranges include from 0.001 weight percent to 20 weight percent, from 0.001 to 10 weight percent, from 0.01 to 5 weight percent, or even from 0.01 to 2 weight percent.

The upper limitation of the concentration of the fluorinated alkoxy acid does not arise from any inherent limitation of the contacting or separating steps, but rather relate to the solubility of the fluorinated alkoxy acid in the first solution. The lower limitation, similarly, does not arise from an inherent limitation of the contacting or separating steps, but rather relates to the state of the art detection limits of the available analytical techniques. Thus, one of ordinary skill in the art will understand that a proper upper concentration limit will depend on the specific identity of the selected fluorinated alkoxy acid and a proper lower concentration limit will depend on the analytical method available for measurement.

Furthermore, the ratio of fluorinated alkoxy acid to perfluorinated alkanoic acid in the first solution may range from 1:1 to 1,000,000:1.

Second Solution

In the method described herein, contacting the first solution with an anion-exchange resin produces a second solution and a resultant anion-exchange resin having perfluorinated alkanoic acid adsorbed thereto, wherein the perfluorinated alkanoic acid is present in the first solution at a first concentration (discussed above) and is present in the second solution at a second concentration which is lower than the first concentration.

The second solution, may be further contacted in additional contacting steps, as discussed herein.

The perfluorinated alkanoic acid is present in the second solution in a second concentration which is lower than the first concentration. In some embodiments, the perfluorinated alkanoic acid may be present in from 0 to 0.001 weight percent (based on the total weight of the first solution) (corresponding to 1 ppm); from 0 to $2.5 \times 10^{-6}$ weight percent (corresponding to 25 ppb), or even from 0 to $1 \times 10^{-6}$ weight percent (corresponding to 10 ppb).

The ratio of the first concentration (in the first solution) to the second concentration (in the second solution) of perfluorinated alkanoic acid may range from 10:1 to 1,000,000:1. In some instances, the perfluorinated alkanoic acid is completely removed from the second solution (that is, its concentration is below the detection limits for measuring the concentration in the second solution).

As mentioned herein, the second solution may be further subjected to an additional contacting step to yield a third solution and a second resultant anion-exchange resin having perfluorinated alkanoic acid adsorbed thereto, wherein the perfluorinated alkanoic acid is present in the second solution at a second concentration and is present in the third solution at a third concentration which is lower than the second concentration. Additional contact steps may be further carried out.

Of course, if the second concentration of perfluorinated alkanoic acid is below the detection limits for measuring the concentration in the second solution, it will be difficult to ascertain whether further reduction in concentration has occurred in the third solution. If one were interested in further measuring the concentration in the third solution in such an instance one may, for example, up-concentrate the third solution and measure the concentration of perfluorinated alkanoic acid after such up-concentration. If, however, removing the perfluorinated alkanoic acid to below the detection limits available for the second solution is acceptable for the purposes of carrying out the method, then no further contacting need be performed.

Anion-Exchange Resin

Anion-Exchange resins used the methods described herein include basic resins, particularly, strong basic anion-exchange resins. Strong basic anion-exchange resin may be type 1 (e.g., containing a quaternized ammonia functional group) or type 2 (e.g., obtained by the reaction of styrene-divinyl benzene copolymer with dimethylethanolamine). Type 2 strong basic anion-exchange resins have lower basicity than type 1. Type 2 strong basic anion-exchange resins are generally more efficiently regenerated than type 1 and have a better operating capacity, but their chemical stability may not be as good. Type 1 strong basic anion-exchange resins tend to be more stable in high temperature applications. Examples of strong basic anion-exchange resins that are commercially available include those available under the Dowex, Amberlyst, Ambersep, Ambersorb, Amberlite, Amberjet brands (Dow Chemical Company), Lewatit (Lanxess) or Purolite (Purolite).

The anion-exchange resin employed may have a Gaussian distribution of bead sizes about the average bead diameter or the beads may be monodisperse e.g. Lewatit MonoPlus series or Dowex Monosphere series.

The basic anion exchange resin can have different counter ions like $Cl^-$, $F^-$, $OH^-$ or the like. In some embodiments, the counter ion is the anion of the fluorinated alkoxy acid. The process of loading the ion exchange resin with the proper counter ion is known to a man skilled in the art.

Contacting Process

The perfluorinated alkanoic acid is removed from the first solution containing it by contacting the first solution with an anion-exchange resin to produce a second solution and a resultant anion-exchange resin having fluorinated alkoxy acid adsorbed thereto.

In the methods described herein, the step of contacting the first solution with an anion-exchange resin may take place in one of several ways. First, the anion-exchange resin may be packed into a column. The first solution may thereby be added to the column, allowing it to flow over the anion-exchange resin. Such flow of the first solution may be gravity flow. The flow through the column may be top down or bottom-up. The flow rate is at least 0.1 bed volumes per hour and up to 10 bed volumes per hour, from 0.5 to 8 bed volumes per hour or from 1 to 5 bed volumes per hour. The flow rate may be increased by extending the fresh eluent filled column above the top of the stationary phase or decreased by the tap controls. Faster flow rates can also be achieved by using a pump or by using compressed gas (e.g., air, nitrogen, or argon) to push the first solution through the column. One of ordinary skill in the art will realize that the particle size of the stationary phase must be selected accordingly.

In another embodiment, the step of contacting the first solution with an anion-exchange resin may comprise placing the anion-exchange resin into a water-permeable container (i.e., a bag) and bringing the first solution into contact with such water-permeable container. The water-permeable container containing the anion-exchange resin may, for instance, be added to a vessel containing the first solution. In the alternative, the first solution can be added to a vessel that contains the anion-exchange resin containing water-permeable containers.

In yet another embodiment, the step of contacting the first solution with an anion-exchange resin may include directly contacting the first solution with loose (i.e., unpacked and unpackaged) anion-exchange resin particles. Such direct contact may, for instance, take the form of adding the first solution to a vessel comprising loose anion-exchange resin (i.e., directly added resin particles). Alternatively, such direct contacting may comprise adding loose anion-exchange resin to a vessel containing the first solution.

With any of the methods described herein (especially any of the contacting steps described herein), the anion-exchange resin may first be pre-loaded with a fluorinated alkoxy acid before contacting with the first solution. Such pre-loaded fluorinated alkoxy acid may be the same or different than the fluorinated alkoxy acid in the first solution. In another embodiment, the anion-exchange resin is contacted with the first solution without any such pre-loading or other modification. The fluorinated alkoxy acid is taken up by the anion-exchange resin by which the resin becomes loaded with the anionic surfactant. The anion-exchange resin may be partially loaded, loaded to at least about 50% to at least about 70%, to at least about 80%, to at least about 90%, to at least about 95%, or it may be completely loaded. Complete loading (100% loading) is achieved if substantially no additional fluorinated alkoxy acid is taken up any more from the loading medium. The degree to which the resin is loaded can be adapted based upon, for instance, (i) the amount of perfluorinated alkanoic acid in first solution, (ii) the amount of fluorinated alkoxy acid in the first solution, (iii) the volume of first solution treated, and (iv) the relative adsoption affinity between the anion-exchange resin and (i) the perfluorinated alkanoic acid versus (ii) the fluorinated alkoxy acid. Loading of the resin is typically done by contacting the anion-exchange resin with a solution containing the fluorinated alkoxy acid in a sufficient concentration and for a sufficient time to achieve loading of the resin to the desired degree.

The anion-exchange resin may be in a "non-fixed resin bed" or in a "fixed resin bed". In a fixed resin bed the anion-exchange resin is not agitated. Fixed resin bed typically covers column technology, in which the resin rests and removal of the substance occurs through a chromatographic process. The term non-fixed resin bed is used to indicate that the resin is agitated, for example, being fluidized, stirred or shaken.

The dimension of the anion-exchange resin (e.g., volume of anion-exchange resin containing column) are adapted to the concentration of perfluorinated alkanoic acid and fluorinated alkoxy acid in the first solution and the throughput of first solution to be treated.

Applicants have surprisingly found that the contacting of the first solution with an anion-exchange resin can preferentially remove the perfluorinated alkanoic acid from the first solution over the fluorinated alkoxy acid. This preferential removal arises from a greater affinity of the perfluorinated alkanoic acid for adsorption to the anion-exchange resin compared to the fluorinated alkoxy acid. This may arise from (i) a greater energetic benefit from the interaction of perfluorinated alkanoic acid with the anion-exchange resin (compared to the perfluorinated alkanoic acid) and/or (ii) a greater energetic penalty arising from dissociating the solvent in the first solution from the fluorinated alkoxy acid (compared to the perfluorinated alkanoic acid).

One of ordinary skill in the art will readily understand that the equillibrium of adsorption of perfluorinated alkanoic acid and fluorinated alkoxy acid to the anion-exchange resin may be affected by raising or lowering the temperature of contacting. Accordingly, contacting the first solution with an anion-exchange resin may take place at a temperature of from 10-80° C., selected based upon the method of contacting, and optimized taking into account factors such as, for instance, (i) the degree of separation between the perfluorinated alkanoic acid and the fluorinated alkoxy acid desired, (ii) energy usage, (iii) stability of the anion-exchange resin, (iv) stability of the first solution, and (v) stability of the second solution.

Furthermore, the contacting of the first solution with the anion-exchange resin should be for a time sufficient to reduce the level of perfluorinated alkanoic acid to the desired level in the second solution.

It is also possible to contact the first and/or solution with more than one anion-exchange resins. For example, the first solution may be contacted with a mixture of anion-exchange resins. Further, the second solution may be contacted with an anion-exchange resin as described herein to yield a third solution wherein the concentration of perfluorinated alkanoic acid in the third solution is lower than the concentration of perfluorinated alkanoic acid in the second solution. The resins may be loaded with the same or different ionic surfactant or with the same or different mixtures thereof.

In another embodiment it is possible to use a mixed bed ion exchanger, a mixture of anion and cation exchanger resins, to remove undesired multivalent cations besides the perfluorinated alkanoic acids.

Contacting of the first solution with the resin can be practiced in a so-called batch-wise manner or in a continuous manner. In a batch-wise process, a vessel is charged with the anion-exchange resin and first solution. The mixture in the vessel is then agitated for a time sufficient to reduce the concentration of perfluorinated alkanoic acid to the desired level after which the second solution and anion-exchange resin are separated, e.g. through filtration. The vessel may then be charged anew with first solution and anion-exchange resin and the process is then repeated.

In a continuous process, first solution from which perfluorinated alkanoic acid needs to be removed is continuously added at one end to a vessel, which may or may not be an agitating vessel, that contains anion-exchange resin. Second solution, which has a reduced concentration of perfluoroalkanoic acid is withdrawn at another end of the vessel in a continuous fashion. In a continuous process, the equipment will be designed such that the residence time of the first solution in the vessel is sufficient to reduce the amount of perfluorinated alkanoic acid to the desired level. In a particular embodiment of a continuous process, a plurality, e.g. 2 or more, (preferably agitating) vessels each charged with anion-exchange resin may be used. Accordingly, first solution may be continuously added and second solution withdrawn from the first vessel. The second solution from the first vessel may be fed continuously in the next vessel from which a third solution is continuously withdrawn. This process can be further repeated if more than 2 vessels are used. If a plurality of vessels is used, they are typically arranged in a cascading arrangement.

Removing Acids from Anion-Exchange Resin

Adsorbed perfluorinated alkanoic acid may be removed from the resultant anion-exchange resin by eluting the anion exchange resin according to the processes disclosed in for example U.S. Pat. No. 4,282,162, WO 01/32563 and EP 1 069 078 and the perfluorinated alkanoic acid may then be recovered from the eluate (or the eluate may be incinerated).

The method of removing adsorbed perfluorinated alkanoic acid from the anion-exchange resin disclosed in U.S. Pat. No. 4,282,162 involves eluting the resin with a mixture of a mineral acid and an organic solvent in which water can be dissolved such as for example methanol.

The method of removing adsorbed perfluorinated alkanoic acid from the anion-exchange resin disclosed in WO 01/32563 involves eluting an anion-exchange resin with a mixture of ammonia and a water miscible organic solvent that has a boiling point of less than 150° C.

In the method of removing adsorbed perfluorinated alkanoic acid from the anion-exchange resin disclosed in EP 1 069 078, the anion exchange-resin is eluted with a mixture of water, an ammonium fluoride, ammonium chloride, alkali fluoride or alkali chloride and an organic solvent in which water and the halide can be dissolved.

To recover the perfluorinated alkanoic acid from the eluate, the process disclosed in U.S. Pat. No. 5,442,097 can be used.

EXAMPLES

Measurement of Acid Levels in Aqueous Solution

The concentration of the fluorinated alkoxy acid was measured on a Agilent 6890A gaschromatograph after esterification with Methanol.

For the measurement of the amount of the alkanoic acid in the fluorinated alkoxy acid the fluorinated alkoxy acid had to be diluted with Methanol to a concentration of 10 µg/ml. This sample was analyzed on an Agilent 1100 HPLC, coupled with an ABSciex 4000 Q-Trap Triple Quadrupol Mass Spectrometer.

Example 1

A glass-column was filled with 300 ml Dowex 22-resin in the OH⁻ form (a strong basic resin). The Dowex 22-resin was first completely loaded with pure $CF_3OCF_2CF_2CF_2OCHFCF_2CO_2NH_4$ and rinsed with water. Then a first solution of $CF_3OCF_2CF_2CF_2OCHFCF_2CO_2NH_4$ (0.5 weight percent based on the total weight of the solution) and $CF_3(CF_2)_6CO_2NH_4$ (0.0017 weight percent based on the total weight of the solution) in water was passed through the column at a rate of 1 to 2 bed volumes per hour. After 70 bed volumes, the $CF_3(CF_2)_6CO_2NH_4$ level was still below the detection limit (<25 ppb).

The invention claimed is:

1. A method for preferentially removing a perfluorinated alkanoic acid from a first solution containing the perfluorinated alkanoic acid and a first fluorinated alkoxy acid, the method comprising pre-loading an anion-exchange resin with a second fluorinated alkoxy acid, which may be the same or different than the first fluorinated alkoxy acid, to form a pre-loaded anion-exchange resin, contacting the first solution with the pre-loaded anion-exchange resin and preferentially removing the fluorinated alkanoic acid relative to the first fluorinated alkoxy acid to produce a second solution and a resultant anion-exchange resin having the perfluorinated alkanoic acid adsorbed thereto, wherein the perfluorinated alkanoic acid is present in the first solution at a first concentration and is present in the second solution at a second concentration which is lower than the first concentration, and separating the second solution from the resultant anion-exchange resin.

2. The method of claim 1, wherein the ratio of the first concentration to the second concentration is from 10:1 to 1,000,000:1.

3. The method of claim 1, wherein the first fluorinated alkoxy acid is present in the first solution at a concentration of from 10 to 1000 times the first concentration of perfluorinated alkanoic acid.

4. The method of claim 1, wherein the first solution contains a solvent.

5. The method of claim 4, wherein the solvent is water.

6. The method of claim 1, further comprising removing the adsorbed perfluorinated alkanoic acid from the resultant anion-exchange resin.

7. The method of claim 6, wherein removing comprises contacting the resultant anion-exchange resin with a mixture of organic alcohol and water.

8. The method of claim 1, further comprising incinerating the resultant anion-exchange resin.

9. The method of claim 1,
wherein the perfluorinated alkanoic acid is selected from a perfluorinated alkyl carboxylic acid and a perfluorinated alkyl sulfonic acid.

10. The method of claim 9, wherein the perfluorinated alkyl carboxylic acid has from 6 to 12 carbon atoms and the perfluorinated alkyl sulfonic acid has from 6 to 12 carbon atoms.

11. The method of claim 1,
wherein the perfluorinated alkanoic acid has from 4 to 12 carbon atoms.

12. The method of claim 11, wherein the perfluorinated alkanoic acid has from 8 to 12 carbon atoms.

13. The method of claim 12, wherein the perfluorinated alkanoic acid has from 8 to 9 carbon atoms.

14. The method of claim 11, wherein the perfluorinated alkanoic acid is selected from a perfluorinated alkyl carboxylic acid and a perfluorinated alkyl sulfonic acid.

15. The method of claim 1, wherein the anion-exchange resin is completely pre-loaded with the second fluorinated alkoxy acid.

* * * * *